United States Patent [19]

Korhummel

[11] Patent Number: 6,046,339
[45] Date of Patent: Apr. 4, 2000

[54] PROCESS FOR THE PREPARATION OF 1, 8-NAPHTHOSULTAM

[75] Inventor: Claus Korhummel, Grenzach-Wyhlen, Germany

[73] Assignee: Ciba Specialty Chemicals Corporation, Tarrytown, N.Y.

[21] Appl. No.: 09/297,518

[22] PCT Filed: Oct. 29, 1997

[86] PCT No.: PCT/EP97/05972

§ 371 Date: May 3, 1999

§ 102(e) Date: May 3, 1999

[87] PCT Pub. No.: WO98/21192

PCT Pub. Date: May 22, 1998

[30] Foreign Application Priority Data

Nov. 8, 1996 [GB] United Kingdom .................. 9623304

[51] Int. Cl.[7] .................................................. C07D 275/04
[52] U.S. Cl. .......................................... 548/208; 548/206
[58] Field of Search ..................... 548/206, 207, 548/208

[56] References Cited

FOREIGN PATENT DOCUMENTS

97/36884 10/1997 WIPO .

OTHER PUBLICATIONS

J Phys Chem "Multiple Fluorescences. 6. The Case of 1,8–Naphthosultam" by Kosower vol. 86 pp. 3776–3780, 1982.

J Org Chem "The Pyrolysis of 2H–Naphth[1,8–cd]isothiazole 1,1–dioxide and its 2–Phenyl Analog" by De Jongh vol. 37, No. 13 pp. 2152–2152, 1972.

CA:89 129502 abs of SU 614104, Jul. 1978.

Chem. Abstr. vol. 1, No. 23, 2884, for J. Am. Chem. Soc., Vol. 29, pp. 1319–1328 (1907).

Derwent Abstr. 88–351877 for SU 1397441 (1988).

Derwent Abstr. 73–80309u for SU 379576 (1973).

*Primary Examiner*—Gary Geist
*Assistant Examiner*—Jean F Vollano
*Attorney, Agent, or Firm*—Kevin T. Mansfield

[57] ABSTRACT

The present invention provides a process for the production of 1,8-naphthosultam comprising reacting 1-naphthylamine-8-sulfonic acid with excess $POCl_3$ or $PCl_3$ in the presence, as a proton acceptor, of a mono-, di-, or preferably tri-$C_1$–$C_4$ alkylamine, and in the presence, as a reaction solvent, of mono-, di-, or tri-$C_1$–$C_4$ alkylbenzene.

17 Claims, No Drawings

PROCESS FOR THE PREPARATION OF 1, 8-NAPHTHOSULTAM

This application is the national phase of PCT/EP97/05972 filed Oct. 29, 1997.

The present invention relates to a process for the production of 1,8-naphthosultam.

Various procedures are already known for the production of 1,8-naphthosultam. For example, in Russian Patent No. 379576, 1,8-naphthosultam is produced by the dehydration of 1-naphthylamine-8-sulfonic acid using $POCl_3$ or $PCl_3$ in nitrobenzene at 140°–150° C., the characteristic feature of the process being that the dehydration is conducted in the presence of calcined potash. Russian Patent No. 1397441 describes the production of 1,8-naphthosultam by reacting 1-naphthylamine-8-sulfonic acid with $POCl_3$ in chlorobenzene at 110°–125° C. in the presence of a pyridine compound. Further, Russian Patent No. 614104 describes the production of 1,8-naphthosultam by dehydrating 1-naphthylamine-8-sulfonic acid with $POl_3$ in chlorobenzene at 130° C. in the presence of the disodium salt of 1,1'-dinaphthylmethane-6,7'-disulfonic acid, as dispersant.

Each of these known processes, however, suffers from one or more disadvantages, in particular the need to use high reaction temperatures and/or the use of a reaction solvent or proton acceptor which is hazardous, from the handling, safety or toxicological standpoint, when used in large-scale production processes. Undesired side-reactions, in particular the formation of polymeric sulfonamides, may also be observed in the known processes.

The object of the present invention is to provide a new process for the production of 1,8-naphthosultam which is free from the disadvantages associated with prior processes.

Accordingly, the present invention provides a process for the production of 1,8-naphthosultam comprising reacting 1-naphthylamine-8-sulfonic acid with excess $POCl_3$ or $PCl_3$ in the presence, as proton acceptor, of a mono-, di- or, preferably, tri-$C_1$–$C_4$alkylamine, and in the presence, as reaction solvent, of a mono-, di-or tri-$C_1$–$C_4$alkylbenzene.

$POCl_3$ is preferably used as the dehydrating agent for 1-naphthylamine-8-sulfonic acid.

The proton acceptor used according to the process of the present invention may be a mono-$C_1$–$C_4$alkylamine, such as methylamine, ethylamine, n-propylamine or n-butylamine. Di-$C_1$–$C_4$alkylamines, e.g., dimethylamine, diethylamine, di-n-propylamine or di-n-butylamine, may also be used. It is preferred, however, to use a tri-$C_1$–$C_4$alkylamine, such as trimethylamine, tri-n-propylamine, tri-n-butylamine or, especially, triethylamine, as the proton acceptor.

As a mono-$C_1$–$C_4$alkylbenzene solvent in the process of the present invention, there may be used, e.g., toluene, ethylbenzene, n-propylbenzene, isopropylbenzene or t-butylbenzene. Di-$C_1$–$C_4$alkylbenzenes, e.g., xylenes, diethylbenzenes, di-n-propylbenzenes or di-n-butylbenzenes, may also be used. Tri-$C_1$–$C_4$alkylbenzenes include, e.g., mesitylene. The preferred solvents are toluene and, especially, mesitylene.

The process according to the present invention is conveniently conducted by dissolving 1-naphthylamine-8-sulfonic acid in the reaction solvent and then reacting the 1-naphthylamine-8-sulfonic acid, in the presence of a proton acceptor, with excess $POCl_3$ or $PCl_3$ at an elevated temperature. Unreacted $POCl_3$ or $PCl_3$ is conveniently hydrolysed to phosphoric acid by adding an aqueous medium, such as ice-water or dilute aqueous sodium hydroxide solution. The precipitated crude 1,8-naphthosultam so obtained may then be separated by filtration and dried. If desired the crude 1,8-naphthosultam may be purified by recrystallisation from a suitable solvent, e.g. toluene.

In an alternative reaction sequence, the $POCl_3$ or $PCl_3$ may be first dissolved in the reaction solvent and, to this solution, there may then be added a suspension of the 1-naphthylamine-8-sulfonic acid in the reaction solvent, in the presence of a proton acceptor, and the reaction mixture may be worked up as described before.

The process according to the present invention is preferably conducted at an elevated temperature in the range of from 60° to 100° C., preferably at the boiling point of the solvent, namely at 90° C. in the case of the preferred solvent, mesitylene. Reaction temperatures above the preferred range tend to favour the formation of undesired polymer by-products. The process according to the present invention is preferably conducted over a reaction period ranging from 1 to 4 hours, a reaction time of about 1.5 to 2.5, especially of about 2 hours being preferred.

As already indicated, the present process is effected using an excess of $POCl_3$ or $PCl_3$ relative to 1-naphthylamine-8-sulfonic acid. Preferably 3 to 10 moles, more preferably 3 to 5 moles of $POCl_3$ or $PCl_3$ are used per mole of 1-naphthylamine-8-sulfonic acid.

The 1,8-naphthosultam obtained according to the process of the present invention is useful, e.g., as a starting material for the production of various pharmaceuticals such as calcium channel blockers and 5-$HT_2$ antagonists, and finds further use as a cyan coupler in the photographic industry.

The following Examples further illustrate the present invention. Parts and percentages shown therein are by weight unless otherwise stated.

EXAMPLE 1

65 kg of toluene are charged, with stirring at 20° C., into a 160 liter double-jacketed enamel reactor under nitrogen. 1.2 kg of triethylamine are then allowed to run into the reactor at a temperature of 23° C. 9.65 kg (equivalent to 8.7 kg of 100% pure material) of sieved 1-naphthylamine-8-sulfonic acid hydrate are added and the mixture is homogenised for at least 30 minutes.

In the receiver of a washer tower there are provided 50 kg of 30% aqueous sodium hydroxide and 150 liters of water, making a total volume of 180 liters.

17.9 kg of phosphorus oxychloride are placed, under vacuum, into a feeding vessel. The phosphorus oxychloride is allowed to run into the reactor, with very good stirring, over 10 to 15 minutes. Residual phosphorus oxychloride is rinsed from the reactor using 0.2 liter of toluene. The reaction temperature rises by 5° to 6° C.

The washer tower is then set in operation.

Over a period of one hour, while applying good stirring, the reactor is indirectly heated to produce an internal temperature of 80° C.

After the completion of the addition of phosphorus oxychloride, a vigorous emission of carbon dioxide sets in. During the heating period, the gas emission is reinforced by the formation of hydrogen chloride. Heating is continued at 80° C., with good stirring, for a further 2.5 hours.

Excess phosphorus oxychloride is hydrolysed, with good stirring at 80° C., by careful addition of 37.5 kg of water, thereby forming phosphoric acid. The hydrolysis is accompanied by vigorous emission of hydrogen chloride. The reaction temperature rises by 10° C. but this reaction heat is well dissipated by the boiling of the reaction mixture under reflux. After completion of the water addition, the reaction mixture is held at 80° C. for a further hour and then cooled to 20° C., whereupon crude 1,8-naphthosultam is formed as grey crystals. The crude product is filtered and washed, portionwise, with 100 liters of water. The moist presscake is then dried to constant weight at 110° C. in a vacuum drier. In this way, 7.25 kg of dry, crude product are obtained (88.1% theory). Pure 1,8-naphthosultam of m.pt. 178° C. (99% purity by HPLC and NMR) can be obtained by recrystallisation from toluene.

EXAMPLE 2

65 kg of mesitylene are charged, with stirring at 20° C., into a 160 liter double-jacketed enamel reactor under nitrogen. 1.2 kg of triethylamine are then allowed to run into the reactor at a temperature of 23° C. 9.65 kg (equivalent to 8.7 kg of 100% pure material) of sieved 1-naphthylamine-8-sulfonic acid hydrate are added and the mixture is homogenised for at least 30 minutes.

In the receiver of a washer tower there are provided 50 kg of 30% aqueous sodium hydroxide and 150 liters of water, making a total volume of 180 liters.

17.9 kg of phosphorus oxychloride are placed, under vacuum, into a feeding vessel. The phosphorus oxychloride is allowed to run into the reactor, with very good stirring, over 10 to 15 minutes. Residual phosphorus oxychloride is rinsed from the reactor using 0.2 liter of mesitylene. The reaction temperature rises by 5° to 6° C.

The washer tower is then set in operation.

Over a period of one hour, while applying good stirring, the reactor is indirectly heated to produce an internal temperature of 90° C.

After the completion of the addition of phosphorus oxychloride, a vigorous emission of carbon dioxide sets in. During the heating period, the gas emission is reinforced by the formation of hydrogen chloride. Heating is continued at 90° C., with good stirring, for a further 2 hours.

Excess phosphorus oxychloride is hydrolysed, with good stirring at 80° C., by careful addition of 37.5 kg of water, thereby forming phosphoric acid. The hydrolysis is accompanied by vigorous emission of hydrogen chloride. The reaction temperature rises by 10° C. but this reaction heat is well dissipated by the boiling of the reaction mixture under reflux. After completion of the water addition, the reaction mixture is held at 80° C. for a further hour and then cooled to 20° C., whereupon crude 1,8-naphthosultam is formed as grey crystals. The crude product is filtered and washed, portionwise, with 100 liters of water. The moist presscake is then dried to constant weight at 110° C. in a vacuum drier. In this way, 7.25 kg of dry, crude product are obtained (88.1% theory). Pure 1,8-naphthosultam of m.pt. 178° C. (99% purity by HPLC and NMR) can be obtained by recrystallisation from mesitylene.

Similar results are obtained when the triethylamine proton acceptor is replaced by methylamine, ethylamine, n-propylamine, n-butylamine, dimethylamine, diethylamine, di-n-propylamine, di-n-butylamine, trimethylamine, tri-n-propylamine or tri-n-butylamine.

What is claimed is:

1. A process for the production of 1,8-naphthosultam comprising reacting 1-naphthylamine-8-sulfonic acid with excess $POCl_3$ or $PCl_3$ in the presence, as proton acceptor, of a mono-, di- or tri-$C_1$–$C_4$alkylamine, and in the presence, as reaction solvent, of a mono-, di-or tri-$C_1$–$C_4$alkylbenzene.

2. A process according to claim 1 in which the proton acceptor is a tri-$C_1$–$C_4$alkylamine.

3. A process according to claim 1 in which the proton acceptor is triethylamine.

4. A process according to claim 1 in which 1-naphthylamine-8-sulfonic acid is reacted with $POCl_3$.

5. A process according to claim 1 in which the reaction solvent is a mono-$C_1$–$C_4$alkylbenzene.

6. A process according to claim 1 in which the solvent is toluene or mesitylene.

7. A process according to claim 6 in which the solvent is mesitylene.

8. A process according to claim 1 in which the process is conducted by dissolving 1-naphthylamine-8-sultonic acid in the reaction solvent and then reacting the 1-naphthylamine-8-sulfonic acid, in the presence of a proton acceptor, with excess $POCl_3$ or $PCl_3$ at an elevated temperature.

9. A process according to claim 8 in which unreacted $POCl_3$ or $PCl_3$ is hydrolysed to phosphoric acid by adding an aqueous medium.

10. A process according to claim 1 in which the process is conducted by firstly dissolving the $POCl_3$ or $PCl_3$ in the reaction solvent and then adding, to this solution, a suspension of the 1-naphthylamine-8-sulfonic acid in the reaction solvent, in the presence of a proton acceptor.

11. A process according to claim 1 in which the process is conducted at a temperature in the range of from 60° to 100° C.

12. A process according to claim 11 in which the process is conducted at the boiling point of the solvent.

13. A process according to claim 1 in which the process is effected over a reaction period ranging from 1 to 4 hours.

14. A process according to claim 13 in which the process is effected over a reaction period ranging from 1.5 to 2.5 hours.

15. A process according to claim 14 in which the process is effected over a reaction period of about 2 hours.

16. A process according to claim 1 in which the present process is effected using 3 to 10 moles of $POCl_3$ or $PCl_3$ per mole of 1-naphthylamine-8-sulfonic acid.

17. A process according to claim 16 in which 3 to 5 moles of $POCl_3$ or $PCl_3$ are used per mole of 1-naphthylamine-8-sulfonic acid.

* * * * *